United States Patent
Molin et al.

(10) Patent No.: US 9,302,115 B2
(45) Date of Patent: Apr. 5, 2016

(54) APPARATUS AND METHOD FOR QUANTIFICATION OF THE DESYNCHRONIZATION BETWEEN THE CLOCKS OF TWO HBC ACTIVE IMPLANTS

(71) Applicant: SORIN CRM S.A.S., Clamart (FR)

(72) Inventors: Renzo Dal Molin, Chatillon (FR); Ashutosh Ghildiyal, Clamart (FR)

(73) Assignee: SORIN CRM S.A.S., Clamart (FR)

( * ) Notice: Subject to any disclaimer, the term of this patent is extended or adjusted under 35 U.S.C. 154(b) by 0 days.

(21) Appl. No.: 14/257,195

(22) Filed: Apr. 21, 2014

(65) Prior Publication Data
US 2014/0228913 A1 Aug. 14, 2014

Related U.S. Application Data

(63) Continuation of application No. 13/370,200, filed on Feb. 9, 2012, now Pat. No. 8,705,599.

(30) Foreign Application Priority Data

Feb. 9, 2011 (FR) ..................................... 11 51021

(51) Int. Cl.
*H04B 3/46* (2015.01)
*H04B 17/00* (2015.01)
*H04Q 1/20* (2006.01)
(Continued)

(52) U.S. Cl.
CPC .......... *A61N 1/37288* (2013.01); *A61N 1/3962* (2013.01); *A61N 1/37205* (2013.01)

(58) Field of Classification Search
CPC .............. H04J 3/0667; A61N 1/37288; H04N 21/4305
See application file for complete search history.

(56) References Cited

U.S. PATENT DOCUMENTS 4,987,897 A 1/1991 Funke
5,411,535 A 5/1995 Fujii et al.
(Continued)

FOREIGN PATENT DOCUMENTS

WO WO-2007/047681 A2 4/2007

OTHER PUBLICATIONS

Andrei Grebennikov, RF and Microwave Transmitter Design, John Wiley & Sons, Jun. 2011, http://www.wiley-vch.de/publish/en/books/forthcomingTitles/EEOO/0-470-52099-X/.
(Continued)

*Primary Examiner* — Sam K Ahn
*Assistant Examiner* — Fabricio R Murillo Garcia
(74) *Attorney, Agent, or Firm* — Foley & Lardner LLP

(57) ABSTRACT

A method of determining desynchronization between a first implantable medical device and a second implantable medical device. The method includes receiving a synchronization query from the first device at the second device, that is transmitted in response to the first device detecting a predetermined transition of a first clock of the first device, the first clock having a first pulse rate. The method further includes determining a number of pulses of a second clock of the second device occurring between reception of the synchronization query and a predetermined transition of a third clock of the second device, the third clock having the first pulse rate. The second clock has a second pulse rate higher than the first pulse rate. The method further includes determining the desynchronization between the first device and the second device based on the determined number of pulses of the second clock.

18 Claims, 3 Drawing Sheets

(51) Int. Cl.
*A61N 1/372* (2006.01)
*A61N 1/39* (2006.01)

(56) References Cited

U.S. PATENT DOCUMENTS

| | | | |
|---|---|---|---|
| 5,891,180 A | 4/1999 | Greeninger et al. | |
| 2003/0056135 A1* | 3/2003 | Splett et al. | 713/400 |
| 2004/0133390 A1* | 7/2004 | Osorio | A61B 5/0006 702/178 |
| 2004/0220624 A1 | 11/2004 | Ritscher et al. | |
| 2005/0197680 A1 | 9/2005 | DelMain et al. | |
| 2006/0136004 A1 | 6/2006 | Cowan et al. | |
| 2006/0161675 A1* | 7/2006 | Ducharme et al. | 709/231 |
| 2006/0190060 A1 | 8/2006 | Greeninger et al. | |
| 2007/0088394 A1 | 4/2007 | Jacobson | |
| 2007/0088397 A1 | 4/2007 | Jacobson | |
| 2007/0255330 A1 | 11/2007 | Lee et al. | |
| 2008/0046038 A1 | 2/2008 | Hill et al. | |
| 2008/0103719 A1* | 5/2008 | Seong | G01R 31/318552 702/125 |
| 2009/0030484 A1 | 1/2009 | Chambers | |
| 2009/0088821 A1* | 4/2009 | Abrahamson | 607/60 |
| 2010/0228881 A1* | 9/2010 | Williams | H04J 3/0632 709/248 |
| 2011/0190850 A1* | 8/2011 | Reinke et al. | 607/60 |

OTHER PUBLICATIONS

Behzad Razavi, CMOS RF Receiver Design for Wireless LAN Applications, IEEE Radio and Wireless Conferences, RAWCON 99, 1999, http://www.ee.ucla.edu/~brweb/papers/Conferences/RRAWCON99.pdf.

Domine Leenaerts, et al., Circuit Design for RF Transceivers, Springer, 2001, http://books.google.de/books/about/circuit_design_for_RF_transceivers.html?id=OpGBG2E4MSgC&redir_esc=y.

Foreign Search Report Dated Sep. 9, 2011 (Annexe Au Rapport De Recherche Preliminaire Relatif A La Demande De Brevet Francais No. FR 1151021 FA 747771).

Milton Blake Sleeper, Design data for radio transmitters and receivers, Norman W. Henley Publishing Company, 1922, http://books.google.de/books?id=ZsE4m6AAY7UC&redir_esc=y.

* cited by examiner

APPARATUS AND METHOD FOR QUANTIFICATION OF THE DESYNCHRONIZATION BETWEEN THE CLOCKS OF TWO HBC ACTIVE IMPLANTS

CROSS-REFERENCE TO RELATED APPLICATION

This application is a continuation of U.S. patent application Ser. No. 13/370,200, filed Feb. 9, 2012, which claims the benefit of and priority to French Patent Application No. 1151021, filed Feb. 9, 2011. Both U.S. patent application Ser. No. 13/370,200 and French Patent Application No. 1151021 are hereby incorporated by reference in their entireties.

BACKGROUND

The present invention relates to "medical devices" as defined by the 14 June 1993 Directive 93/42/EEC of the Council of the European Communities, and more specifically to the "active implantable medical devices" as defined by the 20 June 1990 Directive 90/385/EEC of the Council of the European Communities, such as those implanted devices that continuously monitor a patient's cardiac rhythm and deliver if necessary to the heart electrical pulses for stimulation, cardiac resynchronization, cardioversion and/or defibrillation in case of a rhythm disorder detected by the device, as well as neurological devices, cochlear implants, devices for pH measurement, and devices for intracorporeal impedance measurement (such as the measure of the transpulmonary impedance or of the intracardiac impedance).

The present invention relates more particularly to devices that implement autonomous implanted capsules that are free of any physical connection to another medical device, which may be implanted (such as the can of a stimulation pulse generator) or not implanted (such as an external programmer or monitoring device for remote monitoring of the patient). Communication between such an autonomous implanted capsule and another medical device is typically conducted by the interstitial tissues of the body and is known as intracorporeal communication or human body communication ("HBC").

These autonomous implanted capsules using HBC signals for communications are for this reason called "leadless capsules" to distinguish them from the electrodes or sensors placed at the distal end of a lead, the lead being traversed throughout its length by one or more conductors connecting by galvanic conduction the electrode or the sensor distal to a generator connected at the opposite, proximal end, of the lead. Such leadless capsules are for example described in U.S. 2007/0088397 A1 and WO Patent Publication No. 2007/047681 A2 (Nanostim, Inc.) or in U.S. Patent Publication No. 2006/0136004 A1 (EBR Systems, Inc.).

These leadless capsules (which for convenience also are referred to herein simply as "capsules") can be epicardial capsules fixed to the outer wall of the heart, or endocardial capsules fixed to the inside wall of a ventricular or atrial cavity. Capsule attachment to the heart wall is usually obtained by a protruding anchoring helical screw, axially extending out of the body of the capsule and designed to penetrate the heart tissue by screwing to the implantation site.

This capsule typically includes detection/stimulation circuitry to collect depolarization potentials of the myocardium and/or to apply electrical pulses to the site where the capsule is located. In such case, the capsule includes an appropriate electrode, which can be included in an active part of the anchoring screw. It can also incorporate one or more sensors for locally measuring the value of a parameter such as the oxygen level in the blood, the endocardial cardiac pressure, the acceleration of the heart wall, the acceleration of the patient as an indicator of activity, etc.

It should be understood however that the present invention is not limited to a particular type of capsule, and is equally applicable to any type of leadless capsule, regardless of its functional purpose.

Of course, for the remote exchange of data, the leadless capsules incorporate transmitter/receiver circuitry for wireless communication. Several techniques have been proposed for wireless communication between the autonomous implanted capsules and a main remote device to centralize the information collected by the capsule and send to the capsule, if necessary, appropriate controls (particularly where the capsule may be an implanted pacemaker, defibrillator or resynchronizer, a subcutaneous defibrillator, or a long-term event recorder).

Thus, U.S. Patent Publication No. 2006/0136004 A1 proposes to transmit data by acoustic waves propagating inside the body. Although this technique is safe and effective, it nevertheless has the disadvantage of requiring a relatively high emitting power given the attenuation of acoustic waves into the body, and therefore allows only relatively low data transmission rates.

U.S. Pat. No. 5,411,535 proposes another communication technique, based on the use of radiofrequency waves (RF). Again, a relatively high transmission power is required, and the attenuation of these waves by intracorporeal tissue is a major barrier to their spread.

Another communication technique has been proposed by U.S. Pat. No. 4,987,897, but it is a data exchange with an external device (programmer), through the patient's skin rather than an intracorporeal transmission. This transmission is over a short distance, between, on the one hand, the housing of a pacemaker implanted in a subcutaneous pocket and, on the other hand, an external programmer placed against the skin near the generator. Currents therefore circulate through the skin in a very distant area from the sensitive areas, particularly in a very distant area from the myocardium, which avoids any risk of disruption of the natural or stimulated depolarization waves of the latter.

The U.S. Patent Publication No. 2007/0088397 A1 also proposes to use the stimulation pulses produced by a capsule as a vehicle for the transmission of data previously collected or created by the capsule. To this purpose, the pulse, instead of presenting a monotonic variation of voltage, is interrupted in a controlled manner for very short durations in order to create (modulate) in the profile of the pulse very narrow pulses whose sequence corresponds to binary encoding of information to be transmitted.

The processing of signals exchanged between the capsules and/or the other medical device (e.g., an implanted pacemaker or defibrillator) or, more generally, between the various independent devices implanted in the patient's body or not, implies to synchronize the respective processing circuits of these devices, or at least to determine their degree of desynchronization. If it is known, such a synchronization parameter may be included in the various signal processing calculations, or serve to apply an appropriate temporal correction to the timing of the received or transmitted signals. This "software synchronization" thus can be achieved which does not need to apply a corrective action or adjustment of the clock circuits of the various devices.

Further, to the extent that the various devices are all physically independent, each has its own clock that provides control of the various circuits, including the circuits for digital signal processing. These independent clocks have a frequency difference which, even if it is small, introduces over time a desynchronization of these devices that becomes necessary to identify and compensate for.

In a related area, U.S. Patent Publication No. 2009/030484 A1 proposes to synchronize the sequencing of two separate hearing aids, arranged on both ears of a patient, to reduce mutual interference that may be generated. These hearing aids are equipped with their own clocks, and with means for exchanging resynchronization data to readjust these two clocks.

The problem of synchronous operation of leadless implants is also discussed by US Patent Publication No. 2007/0255330 A1, which refers to measuring the time interval between the detection in two different regions of the patient of the same physiological event, or by US Patent Publication No. 2005/0197680 A1, which acts on a phase-locked loop for fine control of the clock frequency.

The frequency drift is increased by the fact that, to avoid excessive consumption, the implanted devices use clocks operating at a relatively low frequency (typically in the range of 32 kHz) and thus with a lower temporal resolution (about 30 μs) which does not allow a detailed evaluation of the synchronization timing differences. This is particularly mentioned, as such, by the US Patent Publication No. 2007/0088394 A1, but outside of the context of synchronization between the implants.

Indeed, whatever the technique used, the processing of the received or emitted HBC signal by a capsule requires considerable energy compared to the energy resources available to the capsule. Given its autonomous nature, the capsule can in fact use only its own resources such as an energy harvester circuit (by the movement of the capsule) and/or a small integrated battery, which energy sources are in themselves well known to persons of ordinary skill in the art and form no part of the present invention, and therefore are not described in detail.

The management of the available energy is, however, a crucial point in the implementation of HBC signals to and from autonomous implanted capsules, and it is essential to develop techniques that minimize the energy requirements of these capsules.

SUMMARY

It is, therefore, an object of the present invention to determine an offset between the clocks of two independent medical devices in wireless communications, so as to implement any appropriate remedial actions.

It is a further object of the present invention to address the delay of transmission of the pulses from one device to another.

Broadly, one aspect of the present invention is directed to an apparatus and method for quantifying a desynchronization between two clocks of a system comprising at least one medical device and at least one active implantable medical device of the general type disclosed in US Patent Publication No. 2007/0088397 A1 cited above, which disclosure is incorporated herein by reference, that is to say two devices that wirelessly communicate with each other via intracorporeal communications, preferably using signals consisting of modulated electrical pulse trains carried by the interstitial tissues of the body.

Although the present invention is described in the context and example of using HBC signals for wireless communication, it is not limited to this specific mode of transmission of pulses, and also applies to the case of signals consisting of other types of waves conducted by the interstitial tissues of the body, or of acoustic waves or magnetic or electromagnetic pulses or waves passing through the body.

One embodiment of such a system comprises: a first device comprising a first clock, first signal transmitter/receiver, and a first digital processing circuit that is clocked by the first clock; and a second device comprising a second clock, a second signal transmitter/receiver, and a second digital processing circuit clocked by the second clock. The term "clocked" as used herein means to control the speed at which the respective digital processing circuits operate to process digital data, make calculations, execute instructions, etc., that is a function of the clock pulse period or the corresponding clock pulse rate of the first or second clocks. In this embodiment, one of the first and second devices also comprises a third clock, the third clock having a higher frequency and thus a shorter period and a faster clock pulse rate (or speed) than the first and second clocks, and the first and second clocks have essentially the same period or clock pulse rate. To quantify at the second device a lack of synchronism of the second clock as compared to the first clock, the third clock is used in the following manner:

a) Using the third clock of one of the first and second devices, on a predetermined transition of the second clock, transmitting from the second device to the first device a synchronization query signal;

b) counting the pulses of the third clock that occur from the predetermined transition of the second clock initiating the synchronization query signal until the detection of a predetermined transition of the first clock; then c) transmitting from the first device to the second device a response signal to the synchronization query; and d) at the second device, upon reception of the response signal to the synchronization query, calculating a temporal shift corresponding to a lack of synchronism based on the result of counting the pulses of the third clock.

In a preferred embodiment, the first device includes the third clock, and counting the pulses of the third clock further comprises:

counting the pulses of the third clock until detection of said predetermined transition of the first clock, wherein the response signal to the synchronization request contains the result based on counting the pulses of the third clock.

In an alternate preferred embodiment, the second device includes the third clock and:

the second device counts the pulses of the third clock until the reception of said response signal to the synchronization request.

In either of these two alternative preferred embodiments, the calculation of the lack of synchronization can be achieved, regardless of the propagation time of the conducted electrical pulses between the first and second devices, by application of a relation of the form:

$$\text{OFFSET} = T_{clk} - D,$$

wherein "OFFSET" is the value of a temporal offset corresponding to a lack of synchronization, "$T_{clk}$" is the period of the first and second clocks, and D is a duration corresponding to the result from counting the pulses of the third clock.

In another alternative embodiment of the present inventions one of the first and second devices includes the third clock and the other of the first and second device includes a fourth clock, the fourth clock having the same clock frequency and pulse rate as the third clock, wherein:

Step a) further comprises starting the counting of the pulses of the fourth clock on the predetermined transition of the second clock;

Step b) further comprises the counting the pulses of the third clock until detection of said predetermined transition of the first clock;

The response signal to the synchronization request emitted in step c) contains the result of the counting of the pulses of the third clock; and Step d) includes the calculation of said temporal delay based on the results of both the counting of the pulses of the fourth clock and of the counting of the pulses of the third clock.

In the latter case, the calculation of the desynchronization can be achieved, taking into account the propagation time of the electrical pulses conducted between the first and second devices, by applying a relation of the form:

$$\text{OFFSET} = T_{clk} - \left[\frac{D1 + D2}{2}\right]$$

wherein "OFFSET" is the offset value corresponding to said lack of time synchronization, "$T_{clk}$" is the period of the first and second clocks, D1 is the duration corresponding to the result of counting of the pulses of the third clock, and D2 is the duration corresponding to the result of counting of the pulses of the fourth clock.

Advantageously, in a preferred embodiment of the various embodiments described above, the third and/or fourth clocks are selectively activated and initially deactivated clocks, while the first and second clocks are continuously activated, wherein the method:

in step a) includes a sub-step of activating of the fourth clock before the start of the counting of pulses, and in step d) includes a sub-step of disabling the fourth clock after receiving the response signal to the synchronization request; and/or in step b) includes a sub-step of activating of the third clock before the start of the counting of pulses, and of disabling of the third clock after detection of the predetermined transition of the first clock.

The frequencies of the first and second clocks defining the corresponding periods are preferably equal and second to be between 15 and 50 kHz, more preferably between 30 and 35 kHz, and the fast clock frequencies of the third and fourth clocks are preferably at least 10 times the frequency of the first and second slow clocks. The accuracy of the slow clocks is advantageously better than 1%.

As noted above, the transmission of information takes place by propagation of pulses in the interstitial tissues of the patient's body, and this propagation requires a significant delay. Accordingly, a propagation delay also could be added to the required response time of the low noise amplifier ("LNA") conventionally found in an HBC signal receiver circuit to detect a pulse at the input of the receiver circuit.

These two added delays lead to a "transmission time" that most often cannot be ignored, and which is in addition to the proper synchronization of the clocks.

It should be understood that while the result may be a count of the number of fast pulses occurring during the defined period of time, in the alternative the result may be a value corresponding to the counted number of pulses, or it may be a value corresponding to a duration of time that is based on the number of pulses counted during the defined period. The precise data constituting the result transmitted is a matter of design choice based on the signals being used to transmit the result from one device to another.

Another aspect of the present invention is directed to a medical device that can be used in a system of the type described above involving at least two medical devices, such that the one medical device has the capability to communicate wirelessly with system to determine a quantification of its desynchronization with the system with which its communicates. One such embodiment is directed to an active implantable medical device able to communicate wirelessly by pulse trains conducted by interstitial tissues of a patient (HBC signals) with at least one other medical device, including apparatus for quantifying a desynchronization of said active implantable medical device from said other medical device, comprising:

a transmitter/receiver of HBC signals;

a slow clock having a slow clock rate signal having pulses including transitions;

a first digital signal processing circuit;

means responsive to a predetermined transition of said slow clock for transmitting a first HBC signal that is a synchronization query signal (SYNC);

means for receiving a second HBC signal that is a response to a SYNC signal, including a first count of pulses of a fast clock rate signal occurring during a period corresponding to a period of said slow clock rate signal, the fast clock rate signal have a faster pulse clock rate than said slow clock; and means for computing a temporal shift (OFFSET) corresponding to said desynchronization based on said first count.

In a preferred embodiment, the means for computing the temporal shift based on said first count applies the relation of the form:

$$T_{clk} = \text{OFFSET} - D_1$$

wherein OFFSET is a temporal shift value corresponding to said desynchronization, $T_{clk}$ is a period of the slow clock rate signal and D is a duration corresponding to the count of the fast clock rate signal pulses.

Preferably, the active implantable medical device further comprises:

a second clock having said fast clock pulse rate signal having pulses and transitions;

means for determining a second count corresponding to a number of pulses of said second clock fast clock pulse rate signal occurring during a period between the transmission of the first HBC signal and the receipt of the second HBC signal;

wherein the means for computing the temporal shift further comprises means for computing said temporal shift based on said first count and said second count.

Further, in this embodiment the means for computing the temporal shift applies the relation of the form:

$$\text{OFFSET} = T_{clk} - \left[\frac{D1 + D2}{2}\right]$$

wherein OFFSET is a value shift value corresponding to said desynchronization, $T_{clk}$ is the period between the slow clock rate signal pulses, D1 is the duration corresponding to the first count and D2 is the duration corresponding to the second count.

In one embodiment, the active implantable medical device is a capsule wherein said second clock has an active state and an inactive state further comprising means for placing said second clock in an active state in response to a transmitted first HBC signal, and for placing said second clock in an inactive state in response to a receipt of said second HBC signal.

Yet another aspect of the present invention is directed to a medical device that can be used in a system of the type described above involving at least two medical devices, such that the one medical device has the capability to communicate wirelessly with system and provides data to the system to permit the other medical devices in the systems to determine their quantification of desynchronization with the system. One such embodiment is directed to a medical device able to communicate wirelessly by pulse transition conducted by interstitial tissues of a patient (HBC signals) with at least one active implantable medical device, an apparatus for use in quantifying desynchronization of said active implantable medical device from said medical device comprising:

a transmitter/receiver of HBC signals;

a slow clock having a slow clock pulse rate signal having pulses and transitions;

a fast clock having a fast clock pulse rate signal having pulses and transitions, said fast clock pulse rate being faster than the slow clock rate; means responsive to a receipt of a first HBC signal corresponding to a synchronization query (SYNC) from said active implantable medical device for determining a first count corresponding to a number of fast clock rate signal pulses counted during a period between two consecutive pulses of said slow clock pulse rate signal;

means responsive to determining said first count for transmitting a second HBC signal corresponding to a response to said first HBC signal and including said first count.

In a preferred embodiment, the medical device is an active implantable medical device such as a cardiac pacemaker, or defibrillator or a long term recording device.

BRIEF DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

With reference to the drawings, an example of a system and method, and medical devices that are part of such a system, according to preferred embodiments of the present invention will now be described.

Figure 1:
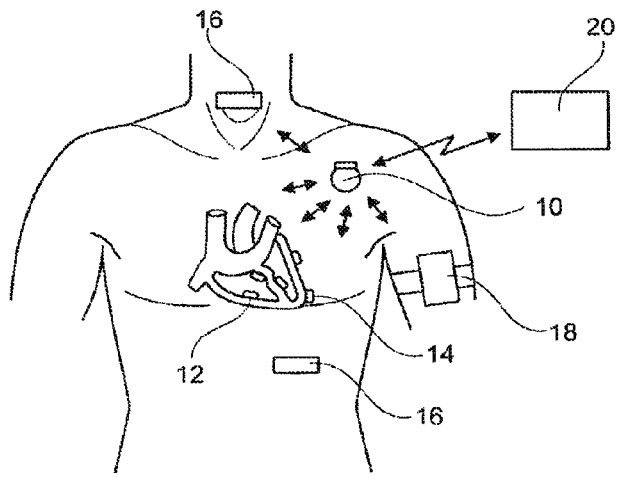
FIG. 1 is a schematic illustration of a system of medical devices including leadless capsules implanted within the body of a patient.

With reference to FIG. 1, a system of medical devices implanted in the body of a patient is shown, communicating with each other through wireless communication of signals through the intracorporeal tissues via human body communication ("HBC").

Implanted in the patient are, for example, an implantable device 10 such as an implantable defibrillator/pacemaker/resynchronizer or a subcutaneous defibrillator or a long-term event recorder. In this embodiment, device 10 is part of a system comprising a plurality of devices 12 to 18, with which device 10 is likely to communicate by HBC. It should be understood that device 10 can also be implanted as a capsule, without requiring the presence of a subcutaneously implanted defibrillator/pacemaker/resynchronizer connected to one or more leads, or a subcutaneous defibrillator.

The devices 12 to 18 may include intracardiac capsules 12 and/or epicardial capsules 14, located directly on the patient's heart. Such capsules are for example described in US Patent Publication No. 2007/0088397 A1, WO 2007/047681 A2 and US Patent Publication No. 2006/0136004 A1, and are attached to the heart wall by a protruding anchoring screw intended to penetrate into the cardiac tissue by screwing at the implantation site. The anchoring screw may be a passive screw, serving only to fix the capsule, or an active screw, serving to fix the capsule as well as to collect the signals of depolarization propagated in myocardium tissues and/or deliver electrical pulses to the implantation site.

The system may also include other devices such as myopotential sensors 16 or neurological stimulation devices, and possibly an external device (18) disposed on an armband and provided with electrodes in contact with skin. The device 10 can be used as a gateway to the outside world to communicate with an external device 20 such as a programmer device or a remote data transmission device with which it can communicate, notably by RF telemetry in the Medical Implants Communication System (MIGS) frequency band 402-405 MHz, or in the 401-402 MHz and 405-406 MHz MEDS frequency bands, or in the public ISM (Industrial, Scientific and Medical) 863-870 MHz, 902-928 MHz and 2.4 GHz frequency bands used by medical devices.

Each of the devices 10 to 18 is provided with at least one pair of electrodes which for the implantable devices are in direct contact with body tissues, or in the case of an external device 18 in contact with the skin or connected to leads or having electrodes on the connector or on the housing for the device 10.

One of the devices, for example, the pacemaker/defibrillator 10 may act as a hub or master device in a star wireless network architecture, in which the various leadless capsules (12) to (18) are slave devices—this for a communication from the pacemaker/defibrillator to the capsule; for a communication in the other direction, the roles are reversed.

The nature of the communication between the different devices, networked or not, and the type of network considered, however, do not form any part of the present invention, which instead concerns only the initial communication between any of the two implanted devices.

The following example of communication between the pacemaker/defibrillator 10 as a master device and an intracardiac capsule 12 as a slave device is provided using HBC signals, but this example is purely illustrative and non limiting and it should be understood that the present invention can be applied to any wireless communication between any two medical devices (10) to (20) described above, and this application is indifferently as to the direction of the communication (that is to say that the roles of master and slave can be reversed).

Figure 2:
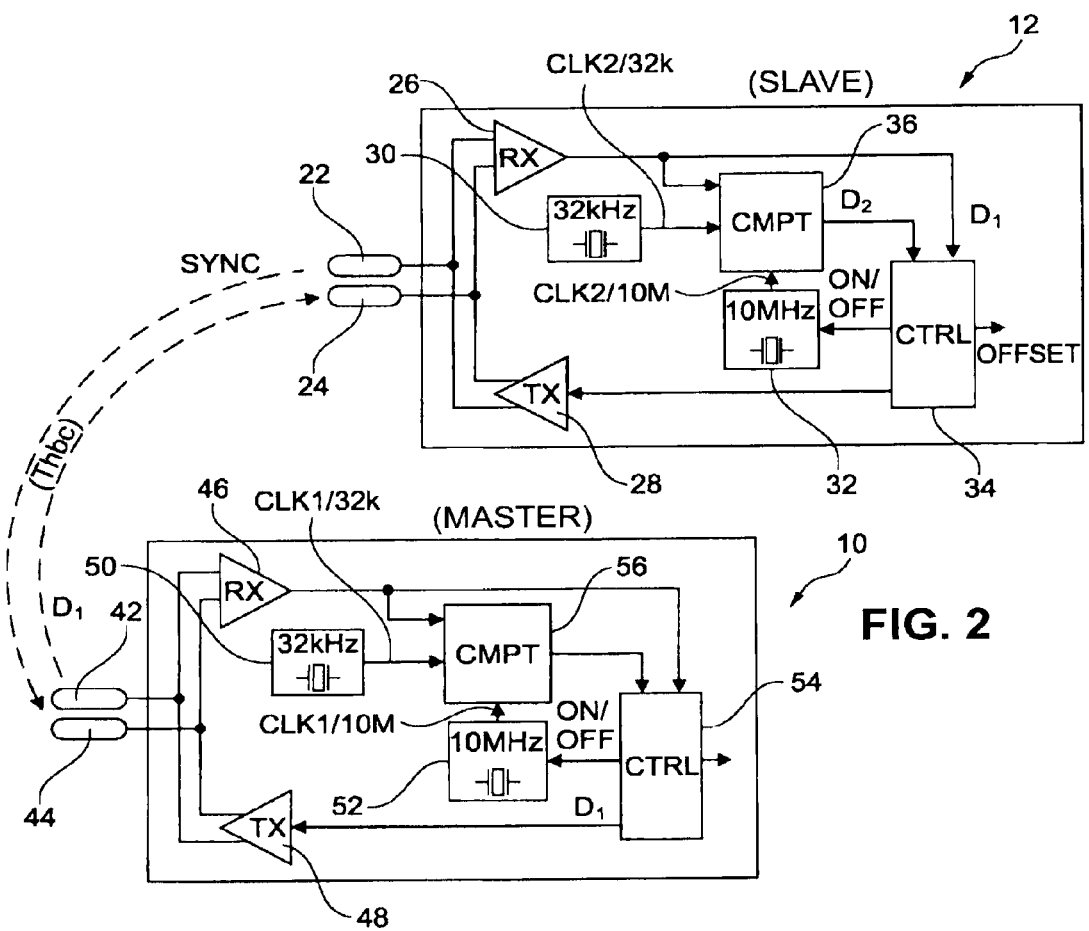
FIG. 2 is a functional block diagram showing the different constituting stages of two devices of the system of FIG. 1 and their communication method.

Referring to FIG. 2, a schematic of the internal circuit of the pacemaker/defibrillator 10 and of the leadless capsule 12 required for the implementation of the present invention is illustrated. In the following designations, only the constituting components 22 to 36 of the leadless capsule 12 are described, and it should be understood that the pacemaker/defibrillator 10 includes similar elements 42 to 56, corresponding to the elements 22 to 36 described in the case of the capsule, that work and function in the same way.

Capsule 12 includes two electrodes 22, 24 in direct contact with body tissues, allowing the transmission and reception of HBC signals consisting of pulses carried by the interstitial tissues of the body located between the two devices 10 and 12 and also used for detection and pacing. For the capsule 12, one of the electrodes 22 or 24 may be constituted by the anchoring screw into the tissue of the heart, or by one of the electrodes on the housing or connected to the housing of the capsule. The pair of electrodes 22, 24 is connected to a receiver circuit (RX) 26 having for example a low noise amplifier (not shown) for detection of the potentials collected between the electrodes and to a transmitter circuit (TX) 28 to produce pulses for communication by HBC signals with the remote device (10). Transmitter (RX) and receiver (RX) circuits are conventional and well known to a person of ordinary skill in the art, and may be combined into an integrated circuit structure. For example, reference here is made to the following publications: as to the design of a receiver "CMOS RF Receiver Design for Wireless LAN Applications": http://www.ee.ucla.edu/-brweb/papers/Conferences/RRAWCON99.pdf; as to the design of an RF transmitter, "RF and Microwave Transmitter Design": http://www.wiley-vch.de/publish/en/books/forthcomingTitles/EE00/0-470-52099-X/; "Design data for radio transmitters and receivers": http://books.google.de/books?id=ZsE4m6AAY7UC&redir_esc=y; and as to the design of RF transceivers which incorporate a transmitter and receiver into a single integrated circuit structure; "Circuit design for RF transceivers"; http://books.google.de/books/about/Circuit_design_for_RF_transceivers.html?id=OpGBG2E4MSgC&redir_esc=y.

The electrodes 22, 24 can also be connected to an electrical pulse generator circuit (not shown) if the capsule 12 incorporates this function and/or to a detection circuit for collection of spontaneous or stimulated cardiac depolarization potentials (these latter potentials are to be distinguished from the potentials corresponding to the HBC signals, the latter of which are emitted at an energy level far below that of cardiac potentials and that of myopotentials of the body). In other words, the electrodes 22, 24 can perform several functions, namely the collection of cardiac potential and/or the stimulation (if applicable), and in any case the transmission/reception for the HBC communication. These detection and collection circuits are well known by those skilled in the art and not involved in the present invention, and therefore have not been illustrated in FIG. 2.

The capsule can also be provided with a sensor such as an acceleration sensor, a pressure sensor, a hemodynamic sensor, a temperature sensor, an oxygen saturation sensor, etc. It is preferably powered by an energy source such as an energy harvester circuit, a small battery, or a combination thereof.

In accordance with one embodiment of the present invention, typically, the device 12 has two separate clocks, namely a slow clock 30 and a fast clock 32. The terms "fast" and "slow" should be understood in their relative sense, that is to say that the clock frequency of fast clock 32 is higher (and the pulse period is shorter) than that of the slow clock 30, preferably with a difference of at least an order of magnitude (ten times).

The slow clock 30 produces pulses CL23 at a frequency of, for example, 32,768 Hz, while the fast clock 32 produces pulses CL21 at a frequency of 9.83040 MHz, that is to say three hundred times that of the slow clock 30. The precise values of these frequencies are given only as non-limiting examples, and were chosen to provide frequencies having a simple, easy to be generated ratio by frequency division. For simplicity of presentation, it is simply referred to "32 kHz" and "10 MHz" frequencies, the precise value chosen being not in itself important for the implementation of the invention. Furthermore, the pulses corresponding to these frequencies of 32 kHz and 10 MHz generated within the device 12 are designated CLK2/32 k and CLK2/10 M, respectively; those generated within the device 10 are designated CLK1/32 k and CLK1/10 M, respectively.

Figure 3:
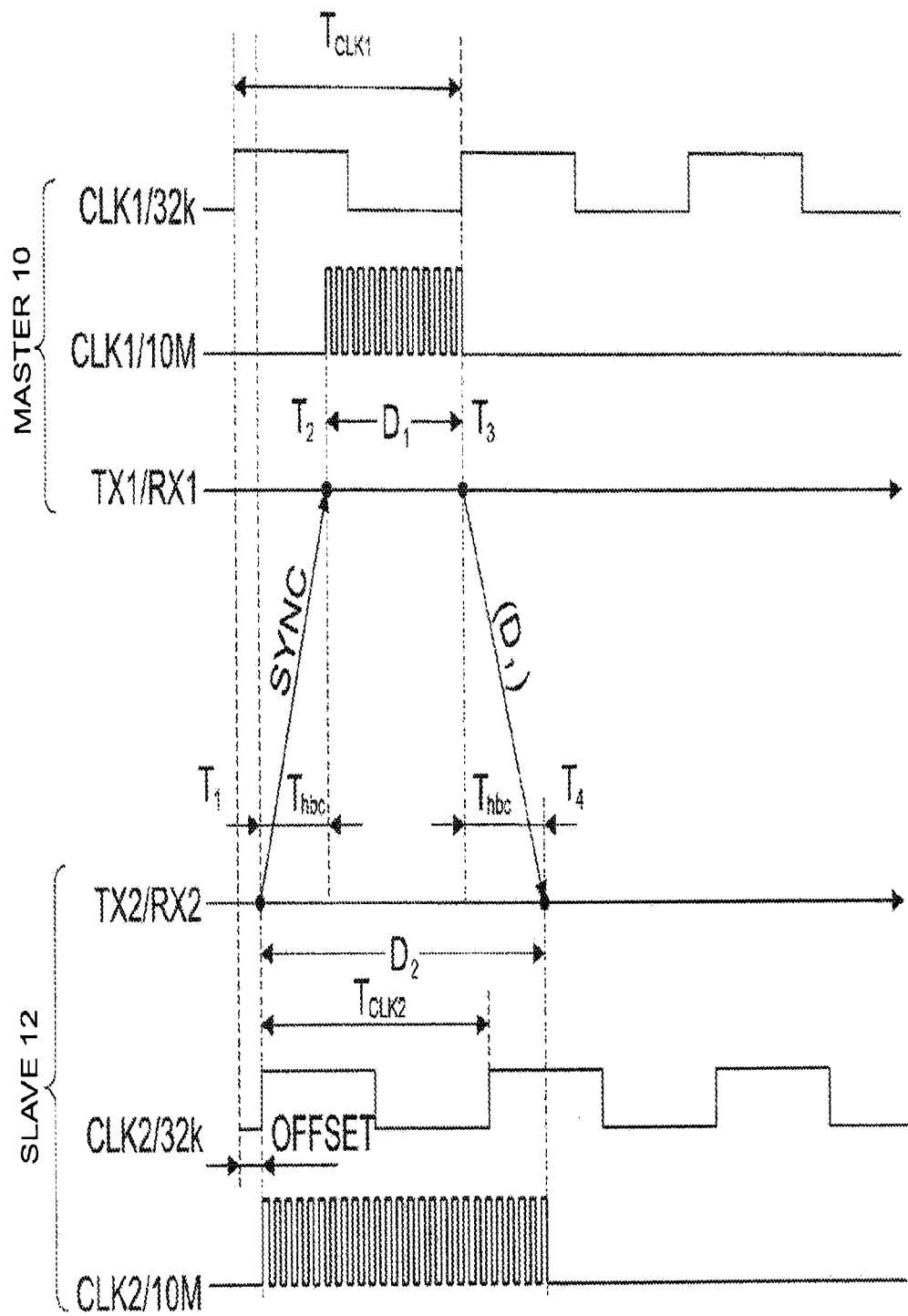
FIG. 3 illustrates a series of timing diagrams representative of a preferred operation for quantifying a desynchronization of the two devices.

The slow and fast clock signals are generated in the form of square wave pulses with a 50% duty cycle, as shown in the timing diagrams in FIG. 3. The corresponding periods are of the order of 30 µs for the slow clock and 0.1 µs for the fast clock.

The slow clock 30 continuously generates pulses, and these pulses are used for the sequencing of a central processing unit, such as a microprocessor or microcontroller (not shown) including all the electronics, memory, registers, etc. for controlling the various functions of the capsule, storing the collected signals, etc. The slow clock 30 thus generates the required clock signals including (i) the analysis of depolarization signals collected by the electrodes, to the generation of the electrical pulses, etc., and (ii) to communication with other implanted devices, including the master device constituted by the implanted pacemaker/defibrillator device 10 in this embodiment.

The fast clock 32, in contrast, is only temporarily activated under the conditions which are described below. The normal state of fast clock 32 is a disabled state, and its activation is controlled by a circuit 34 controlled from data $D_1$ received from the master device 10 and from data $D_2$ developed internally by the slave device 12, including a circuit counter 36 that counts the pulses CLK2/10 M of the fast clock 32. Circuit 36 is controlled by (i) the slow clock 30 and by (ii) HBC signals received from the master device 10.

A relatively low frequency is chosen for clock 30 so as to limit consumption and manage the energy of the devices. For this reason, the fast clock 32 is enabled only when necessary, as its energy consumption is much higher and would be incompatible with its continuous operation, because the energy resources of the device are very limited (in particular, using an energy harvester circuit for the leadless capsule, or a very long life battery (10 years) for the pacemaker/defibrillator 10).

The master device (here the pacemaker/defibrillator) 10 includes the same elements 42 to 56 as the elements (22) to (36) of the slave device constituted by the leadless capsule 12, as mentioned above.

Thus, each of the two representative devices 10 and 12 in this exemplary system is provided with its own slow clock 30 or 50, respectively, which ensures the sequencing of various digital circuits of each of the devices. These two clocks are physically independent, and hence they have some degree of desynchronization or a temporal offset. This offset must be calculated in order to take it into account later in the protocol for the desired operation of the system, in particular so that the windows of reception and transmission of wireless communication between master and slave devices coincide as closely as possible.

The determination of this temporal offset in the slave device 12 will now be described in detail, with reference to FIGS. 3 and 4. On the timing diagrams of FIG. 3, the temporal offset is indicated by the parameter OFFSET (to be determined) and is present between the signals CLK1/32 k and CLK2/32 k of the slow clocks.

Figure 4:
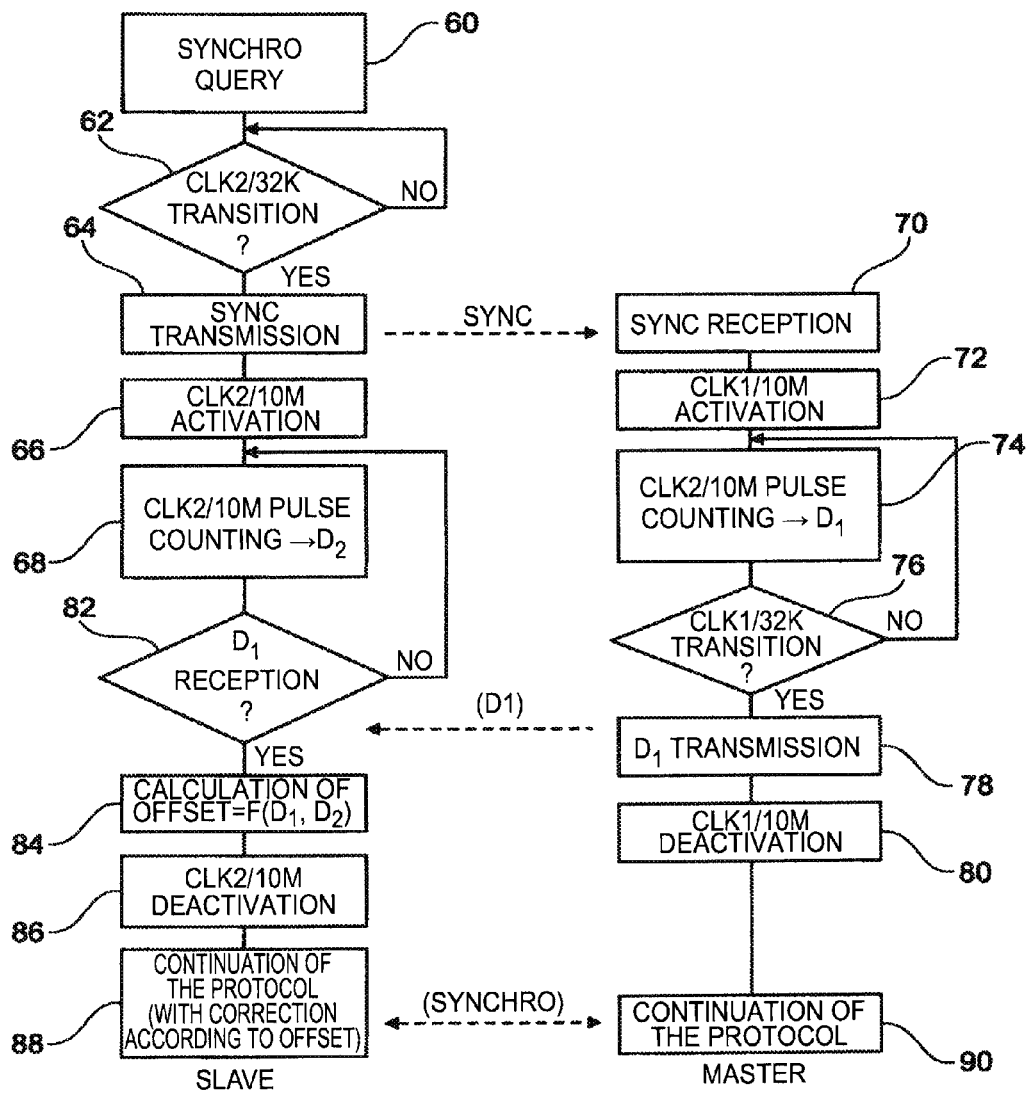
FIG. 4 illustrates, in parallel, two flow chart diagrams corresponding to different steps respectively implemented in each of the two medical devices of FIG. 2 for implementing a preferred embodiment of the present invention.

The slave device 12 which has to be synchronized to the master device 10 waits for a predetermined transition (e.g., a rising edge) of the slow clock signal CLK2/32 k to deliver, at time $T_1$, a synchronization query pulse SYNC towards the master device 10 (steps 60, 62, 64 on the flow chart in FIG. 4).

The master device 10 receives this synchronization query pulse SYNC (step 70) at time $T_2$, with, compared to the moment of transmission, a delay $(T_2-T_1)=T_{hbc}$ corresponding to the transmission time of the pulse through the interstitial tissues of the body from the slave device 12 to the master device 10.

Upon reception of the pulse SYNC, the master device 10 activates its fast clock 52 (step 72), triggered by the control circuit 54 after detection of the SYNC pulse by the receiver circuit 46. The master device 10 then counts the number of pulses CLK1/10 M generated by fast clock 52 by the counting circuit 56 (step 74).

Meanwhile, from the delivery of the pulse SYNC, the slave device 12 activates its fast clock 32 (step 66) and begins to count the pulses CLK2/10 M of the fast clock in its counter circuit 36 (step 68).

At master device 10, the counting of pulses CLK1/10 M of the fast clock continues until detection, at time $T_3$, of a predetermined transition (e.g. a rising edge) of the signal CLK1/32 k of the slow clock 50. The number of pulses counted gives a numerical value of data $D_1$ representative of the duration between the times $T_2$ and $T_3$. With a fast clock signal CLK1/32 k clocked at 10 MHz, the correspondence is of 0.1 μs per counted clock pulse.

This data value $D_1$ is then sent to the slave device 12 in a response message (step 78). Subsequently, the fast clock 52 is turned off (step 80) to limit the energy consumption of the device. The slow clock 50, however, continues to produce the necessary pulses CLK1/32 k for controlling the various digital circuits of the master device 10, in particular for the continuation of the protocol for exchanging data with the slave device 12 as well as its other functions.

At the slave device 12, the response message received back and containing the value $D_1$ is received at time $T_4$, shifted from $T_3$ by a duration corresponding to the transmission time $T_{hbc}$ from the master device 10 to the slave device 12, with a delay $(T_4-T_3)=T_{hbc}$ (assuming that the transmission time is the same in one direction or the other).

Note that the detection circuit 26 of the slave devices is initiated only during the reception window triggered by the fast clock signal CLK2/10 M of the slave device. The duration of this window is a number of periods greater than or equal to one of the periods of signal CLK2/10 M.

Upon reception of the returned response message (step 82), the slave device calculates the OFFSET value from the value received $D_1$ and from $D_2=(T_4-T_1)$ internally calculated and corresponding to the number of pulses CLK2/10 M of the slow clock 30 counted by the counter circuit 36 (step 84).

The fast clock 32 is then deactivated (step 86) to limit the energy consumption and the signal exchange protocol can then be continued (step 88) to exchange signals with the master device 10 (step 90). This communication can be established using the OFFSET parameter and then applying a temporal correction corresponding to the dating of the signals received or transmitted (e.g., a software synchronization).

The offset value OFFSET is calculated as follows. Assuming that the transmission time $T_{hbc}$ is identical in both directions of communication, then:

$$T_4-T_1=2\times T_{hbc}+D_1=D_2$$

$D_2$ and $D_1$ being known ($D_2$ internally counted by the slave device 12 and $D_1$ remotely counted by the master device 10 and transmitted to the slave device (12)), and it can be deduced:

$$T_{hbc}=\frac{D_2-D_1}{2}$$

The crystal oscillators used in these fast and slow clocks to set the operating frequencies have a typical accuracy of 50 ppm, for a frequency of 32,768 Hz. This accuracy is sufficient, on the scale of the transmission of a data packet via HBC signals, which can tolerate a lack of synchronization of a fast clock period due to the tolerance of 50 ppm of quartz. Thus, if $T_{clk1}$ and $T_{clk2}$ respectively denote the periods of the slow clocks 30 and 50 of the slave 12 and master 10 devices, it can be considered that $T_{clk1}=T_{clk2}=T_{clk}$. Thus:

$$T_3-T_1=T_{clk}-\text{OFFSET}=D_1+T_{hbc}$$

hence:

$$\text{OFFSET}=T_{clk}-D_1-T_{hbc}=T_{clk}-\frac{D_1+D_2}{2}$$

The OFFSET shift having thus been calculated, the window of communication with the master device can be determined and adjusted to obtain the desired timing for the transmission of data packet.

Taking into account the propagation time, $T_{hbc}$ is optional, and depends on the desired accuracy. This delay can very roughly be estimated at about 500 ns, so that if the fast clock operates at a frequency of 1 MHz instead of 10 MHz, this delay can be neglected since it has virtually no impact on the calculation result of the OFFSET shift.

In this case, it may be considered that the moments $T_1$ and $T_2$ are mingled, as well as the moments $T_3$ and $T_4$, and thus $D_1=D_2$. As a result, it is no longer necessary to measure $D_2$ (in which case step 68 can be ignored), and directly:

$$\text{OFFSET}=T_{clk}-D_1$$

To the extent that there is no need to measure $D_2$, slave device 12 may be devoid of a fast clock, which simplifies the design, reduces the size and reduces the energy consumption of slave devices.

Alternatively, since $D_1=D_2$, if the slave device 12 is provided with a fast clock, $D_1$ can be evaluated using this fast clock, which gives the value of $D_2$, equal to $D_1$. Even if this solution requires the presence of a fast clock in slave device 12, it simplifies the protocol for exchanging signals with master device 10: indeed, slave device 12 has just to detect the receipt of a marker from master device 10 corresponding to the detection of the transition of the slow clock of the latter, without the need to transmit from the latter a digitized value (i.e., the value of $D_1$).

Generally, master device 10 may simultaneously resynchronize a set of slave devices in a system of such devices by delivering a synchronization pulse on a rising edge of CLK1/32K that is detected by each of the slave devices 14 or 12, for example. Each slave device n starts counting pulses CLKn/10 M at the detection of the synchronization pulse SYNC from a relative master device 10, until the next rising edge of pulse CLKn/32K.

Master device thus 10 preferably maintains slave devices 12 or 14 regularly synchronized by delivering a synchronization pulse SYNC, for example, every 2 ms.

Advantageously, the slave device 12 or 14 may use such a synchronization pulse SYNC as an internal clock. In such a case, slave device 12 or 14 does not need a crystal oscillator as an internal clock. Hence a gain in energy consumption and size results. When the slave device needs to perform particular operations at a faster speed, it can set off (i.e., turn on) a fast resistor-capacitor (RC) circuit having an output pulse signal that acts as a fast clock that it interrupts (deactivates) upon completion of the particular higher speed operation processing.

Advantageously, in one embodiment, the stimulation and the discharge of stimulation capacitors of the master and slave devices can be synchronized to the 2 ms clock of the master device, allowing them to serve as synchronization pulses.

One skilled in the art will appreciate that the foregoing embodiments are provided for purposes of illustration and not of limitation, and that variations in the specific values of parameters provided may be made by persons of ordinary skill in the art without departing from the nature and scope of the present invention.

The invention claimed is:

1. A method of determining a desynchronization between a first implantable medical device (IMD) and a second IMD, the method comprising:
    receiving, by a receiver of the second IMD, a synchronization query (SYNC) from the first IMD, the SYNC being transmitted in response to the first IMD detecting a predetermined transition of a first clock of the first IMD, the first clock having a first pulse rate;
    activating, only upon reception of the SYNC, a second clock of the second IMD, the activating of the second clock being triggered by a control circuit of the second IMD after detection of the SYNC by the receiver of the second IMD;
    determining, by a counting circuit of the second IMD, a number of pulses of the second clock occurring between reception of the SYNC and a predetermined transition of a third clock of the second IMD, the third clock having the first pulse rate, and the second clock having a second pulse rate higher than the first pulse rate, thereby generating a determined number of pulses of the second clock based on the synchronization query and the transition of the third clock;
    activating, after the transmission of the SYNC from the first IMD to the second IMD, a fourth clock of the first IMD;
    sending, to the first IMD, the determined number of pulses of the second clock and turning off the second clock;
    receiving, by a receiver of the first IMD which is initiated only during a reception window triggered by a clock signal of the fourth clock, the determined number of pulses of the second clock; and
    determining, upon reception of the determined number of pulse of the second clock, the desynchronization between the first IMD and the second IMD based on the determined number of pulses of the second clock, then deactivating the fourth clock.

2. The method of claim 1, further comprising:
    determining a number of pulses of the fourth clock of the first IMD occurring between transmission of the SYNC and reception of a response signal to the SYNC, the fourth clock having the second pulse rate; and
    determining the desynchronization between the first IMD and the second IMD based on both the determined number of pulses of the second clock and the determined number of pulses of the fourth clock.

3. The method of claim 2, wherein determining the desynchronization between the first IMD and the second IMD comprises applying a relation of the form:

$$\text{OFFSET} = T_{clk} - [(D_1 + D_2)/2],$$

wherein OFFSET is the value of a temporal offset corresponding to the desynchronization, $T_{clk}$ is the period of the pulse signals of the first and the third clock, $D_1$ is the duration corresponding to the result from determining the number of pulses of the second clock, and $D_2$ is the duration corresponding to the result from determining the number of pulses of the fourth clock.

4. The method of claim 1, wherein the first pulse rate is selected from the range of 15 and 50 kHz.

5. The method of claim 1, wherein the second pulse rate is at least 10 times faster than the first pulse rate.

6. The method of claim 1, wherein determining the desynchronization between the first IMD and the second IMD comprises applying a relation of the form:

$$\text{OFFSET} = T_{clk} - D,$$

wherein OFFSET is the value of a temporal offset corresponding to the desynchronization, $T_{clk}$ is the period of the pulse signals of the first clock, and D is the duration corresponding to the result from determining the number of pulses of the second clock.

7. An active implantable medical device (IMD), comprising:
    an apparatus for providing information to determine a desynchronization between the active IMD and a second medical device, the apparatus comprising:
    a transmitter/receiver of wireless communications;
    a first clock having a first pulse rate; and
    a second clock having a second pulse rate higher than the first pulse rate;
    the apparatus configured to:
        receive, by the receiver of the active IMD, a synchronization query (SYNC) from the second medical device, the synchronization query being transmitted in response to a predetermined transition of a third clock of the second medical device, the third clock having the first pulse rate;
        activate, only upon reception of the SYNC, the second clock of the IMD, the activating of the second clock being triggered by a control circuit of the IMD after detection of the SYNC by the receiver of the IMD;
        determine, by a counting circuit of the IMD, a number of pulses of the second clock of the apparatus occurring between reception of the SYNC and a predetermined transition of the first clock of the apparatus, thereby generating the determined number of pulses of the second clock based on the synchronization query and the transition of the first clock; and
        transmit a response signal comprising the determined number of pulses of the second clock to the second medical device and turn off the second clock;
        wherein the response signal is configured to allow the second medical device to determine, upon reception of the number of pulses of the second clock, the desynchronization between the active IMD and the second medical device based on the determined number of pulses of the second clock;
    wherein a fourth clock of the second medical device is configured to be activated after the transmission of the SYNC from the second medical device and deactivated after determining the desynchronization between the IMD and the second medical device; and wherein a receiver of the second medical device is initiated only during a reception window triggered by a clock signal of the fourth clock and is configured to receive the response signal.

8. The active IMD of claim 7, wherein the first pulse rate is selected from the range of 15 and 50 kHz.

9. The active IMD of claim 7, wherein the second pulse rate is at least 10 times faster than the first pulse rate.

10. The active IMD of claim 7, wherein determining the desynchronization between the active IMD and the second medical device comprises applying a relation of the form:

OFFSET=$T_{clk}$-D, wherein OFFSET is the value of a temporal offset corresponding to the desynchronization, $T_{clk}$ is the period of the pulse signals of the first clock, and D is the duration corresponding to the result from determining the number of pulses of the second clock.

11. The active IMD of claim 7, wherein the active IMD is an autonomous leadless capsule.

12. A non-transitory computer-readable storage medium having instructions stored thereon that, when executed by a processor of an implantable medical device (IMD), cause the implantable medical device to perform operations comprising:

selectively activating, by a control circuit of the IMD, a first clock of the implantable medical device upon reception, at a receiver of the IMD, of a synchronization query (SYNC) from a second medical device, the first clock having a first pulse rate;

determining, by a counting circuit of the IMD, a number of pulses of the first clock of the IMD occurring between reception of the synchronization query and a predetermined transition of a second clock of the IMD, wherein the first pulse rate is higher than a second pulse rate of the second clock, thereby generating the determined number of pulses of the first clock based on the synchronization query and the transition of the second clock;

sending, to the second medical device, the determined number of pulses of the first clock;

wherein the SYNC is transmitted in response to a predetermined transition of a third clock of the second medical device, the third clock having the second pulse rate;

wherein a fourth clock of the second medical device is activated after transmission of the SYNC;

wherein the operations further comprise:
deactivating the first clock of the IMD after detection of the predetermined transition of the second clock; and
determining the desynchronization between the IMD and the second medical device based on the determined number of pulses of the first clock; and wherein the determined number of pulses of the first clock is received by a receiver of the second medical device which is initiated only during a reception window triggered by a clock signal of the fourth clock.

13. The non-transitory computer-readable medium of claim 12, wherein determining the desynchronization between the IMD and the second medical device comprises applying a relation of the form:

OFFSET=$T_{clk}$-D, wherein OFFSET is the value of a temporal offset corresponding to the desynchronization, $T_{clk}$ is the period of the pulse signals of the second clock, and D is the duration corresponding to the result from determining the number of pulses of the first clock.

14. A system for determining a desynchronization between a first implantable medical device and a second implantable medical device, comprising:

a first implantable medical device (IMD) comprising:
a first transmitter/receiver of wireless communications;
a first clock having a first pulse rate; and
a second clock having a second pulse rate higher than the first pulse rate; and a second implantable medical device (IMD) comprising:
a second transmitter/receiver of wireless communications;
a third clock having the first pulse rate; and
a fourth clock having the second pulse rate;

wherein the system is configured to:
detect a predetermined transition of the first clock of the first IMD and in response, transmit a synchronization query (SYNC) to the second IMD;
receive, by a receiver of the second IMD, the SYNC at the second IMD;
activate, only upon reception of the SYNC, the fourth clock of the second IMD, the activating of the fourth clock being triggered by a control circuit of the second IMD after detection of the SYNC by the receiver of the second IMD;
activating, after the transmission of the SYNC from the first IMD to the second IMD, the second clock of the first IMD;
determine, by a counting circuit of the system, a number of pulses of the fourth clock of the second IMD occurring between reception of the SYNC and a predetermined transition of the third clock of the second IMD, thereby generating the determined number of pulses of the fourth clock based on the SYNC and the transition of the third clock;
transmit a response signal comprising the determined number of pulses of the fourth clock from the second IMD to the first IMD and then deactivate the fourth clock;
receiving, by a receiver of the first IMD which is initiated only during a reception window triggered by a clock signal of the second clock, the response signal comprising the determined number of pulses of the fourth clock; and
determine, by the counting circuit or a second counting circuit, a number of pulses of the second clock of the first IMD occurring between transmission of the SYNC and reception of the response signal, thereby generating a determined number of pulses of the second clock based on the SYNC and the response signal, and then deactivate the second clock; and
determine the desynchronization between the first IMD and the second IMD based on both the determined number of pulses of the second clock and the determined number of pulses of the fourth clock.

15. The system of claim 14, wherein at least one of the first IMD and the second IMD is an autonomous leadless capsule.

16. The system of claim 14, wherein the first pulse rate is selected from the range of 15 and 50 kHz.

17. The system of claim 14, wherein the second pulse rate is at least 10 times faster than the first pulse rate.

18. The system of claim 14, wherein determining the desynchronization between the first IMD and the second IMD comprises applying a relation of the form:

$$\text{OFFSET} = T_{clk} - [(D_1 + D_2)/2],$$

wherein OFFSET is the value of a temporal offset corresponding to the desynchronization, $T_{clk}$ is the period of the pulse signals of the first and the third clock, $D_1$ is the duration corresponding to the result from determining the number of pulses of the second clock, and $D_2$ is the duration corresponding to the result from determining the number of pulses of the fourth clock.

* * * * *